(12) United States Patent
Blaeser et al.

(10) Patent No.: US 6,514,281 B1
(45) Date of Patent: Feb. 4, 2003

(54) SYSTEM FOR DELIVERING BIFURCATION STENTS

(75) Inventors: David J. Blaeser, Champlin, MN (US); Richard C. Mattison, Zimmerman, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/148,179

(22) Filed: Sep. 4, 1998

(51) Int. Cl.⁷ .................................................. A61F 2/06
(52) U.S. Cl. ..................................... 623/1.12; 623/1.35
(58) Field of Search ........................... 606/1, 108, 194, 606/195, 198; 623/12, 1.35, 1.11, 1.12, 123

(56) References Cited

U.S. PATENT DOCUMENTS

| | | | |
|---|---|---|---|
| 4,730,616 A | 3/1988 | Frisbie et al. | |
| 4,896,670 A | 1/1990 | Crittenden | |
| 4,994,071 A | 2/1991 | MacGregor | |
| 5,019,085 A | * 5/1991 | Hillstead | 606/198 |
| 5,143,093 A | 9/1992 | Sahota | |
| 5,219,355 A | 6/1993 | Parodi et al. | |
| 5,316,023 A | 5/1994 | Palmaz et al. | |
| 5,405,378 A | 4/1995 | Strecker | 623/1.1 |
| 5,413,581 A | 5/1995 | Goy | |
| 5,571,172 A | 11/1996 | Chin | 623/1.1 |
| 5,591,228 A | 1/1997 | Edoga | |
| 5,607,444 A | 3/1997 | Lam | |
| 5,609,627 A | 3/1997 | Goicoechea et al. | |
| 5,613,980 A | 3/1997 | Chauhan | |
| 5,617,878 A | 4/1997 | Taheri | |
| 5,632,762 A | 5/1997 | Myler | |
| 5,632,763 A | 5/1997 | Glastra | |
| 5,639,278 A | 6/1997 | Dereume et al. | |
| 5,643,340 A | 7/1997 | Nunokawa | |
| 5,669,924 A | 9/1997 | Shaknovich | |
| 5,720,735 A | 2/1998 | Dorros | |
| 5,749,825 A | 5/1998 | Fischell et al. | |
| 5,749,890 A | 5/1998 | Shaknovich | |
| 5,755,734 A | 5/1998 | Richter et al. | |
| 5,755,735 A | 5/1998 | Richter et al. | |
| 5,755,770 A | 5/1998 | Ravenscroft | |
| 5,755,771 A | 5/1998 | Penn et al. | |
| 5,755,772 A | 5/1998 | Evans et al. | |
| 5,755,773 A | 5/1998 | Evans et al. | |
| 5,755,778 A | 5/1998 | Kleshinski | |
| 5,776,101 A | 7/1998 | Goy | |
| 5,782,906 A | 7/1998 | Marshall et al. | |
| 5,797,952 A | * 8/1998 | Klein | 606/198 |
| 5,873,906 A | * 2/1999 | Lau et al. | 606/198 |
| 5,941,908 A | * 8/1999 | Goldsteen et al. | 606/198 |

FOREIGN PATENT DOCUMENTS

| | | |
|---|---|---|
| EP | 0 479 730 B1 | 4/1992 |
| EP | 2 678 508 A1 | 1/1993 |
| EP | 0 686 379 A2 | 12/1995 |
| EP | 696447 | 2/1996 |
| WO | WO 9317636 | 9/1993 |
| WO | 95/21592 | 8/1995 |
| WO | WO 96/34580 | 11/1996 |
| WO | WO 96/41592 | 12/1996 |
| WO | WO 97/07752 | 3/1997 |
| WO | WO 97/15346 | 5/1997 |
| WO | WO 97/41803 | 11/1997 |
| WO | WO 98/19628 | 5/1998 |
| WO | WO 9827894 | 7/1998 |

* cited by examiner

Primary Examiner—Michael H. Thaler
(74) Attorney, Agent, or Firm—Todd P. Messal

(57) ABSTRACT

A stent deployment system includes a tubular member having a first end and a second end and a generally longitudinal opening between the first and second ends. The tubular member has an inner periphery sized to receive a stent therein. A plurality of apertures are disposed on opposite sides of the generally longitudinal opening. An elongate retainer is removably receivable within the apertures to retain the stent in the tubular member and to release the stent from the tubular member when removed from the apertures.

31 Claims, 14 Drawing Sheets

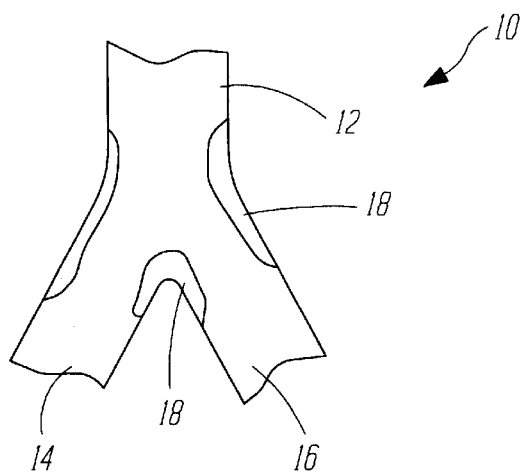
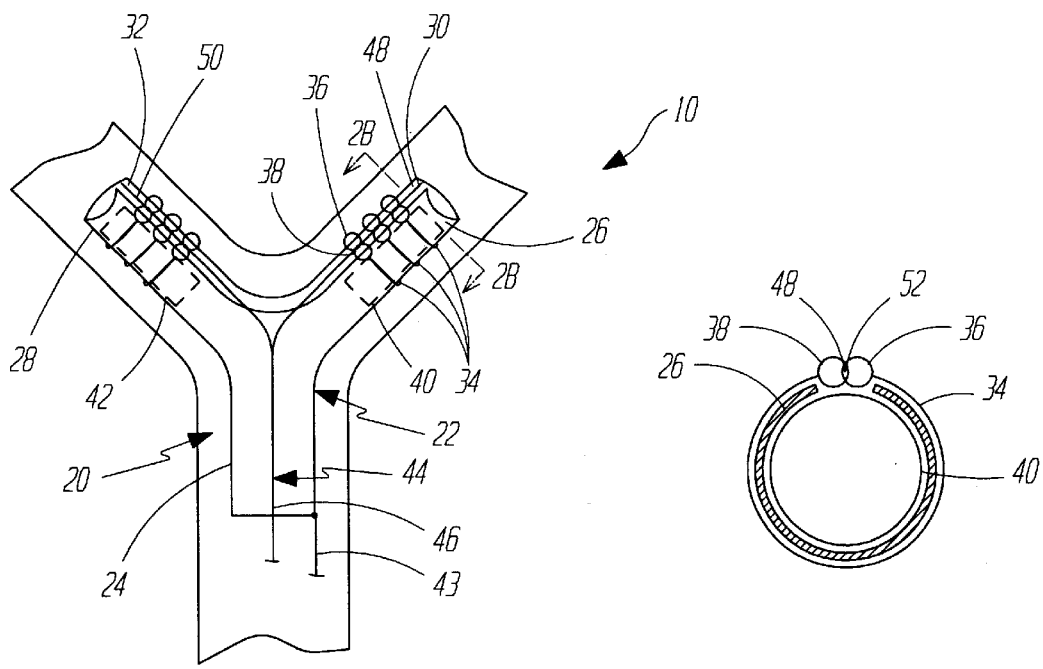

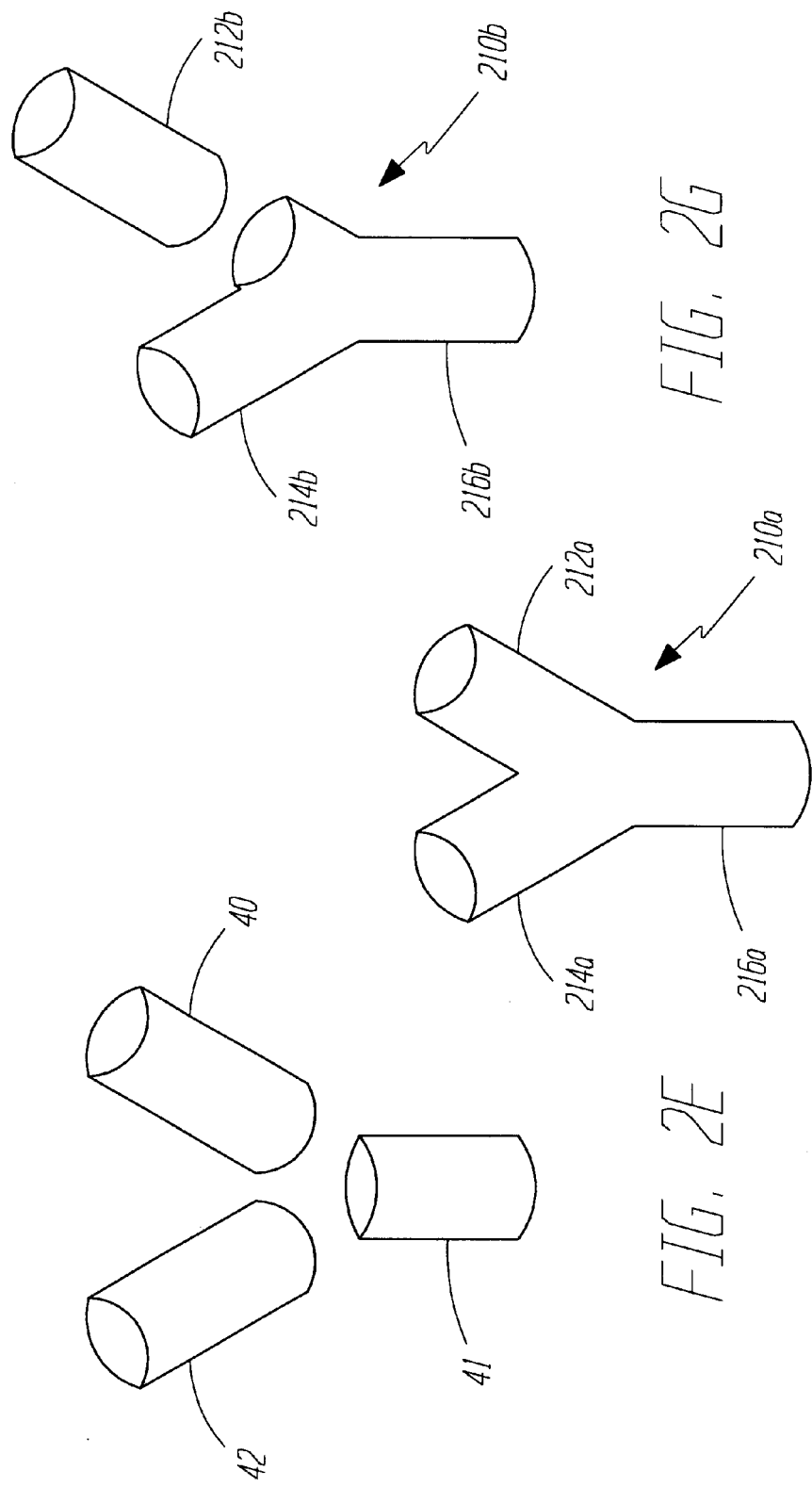

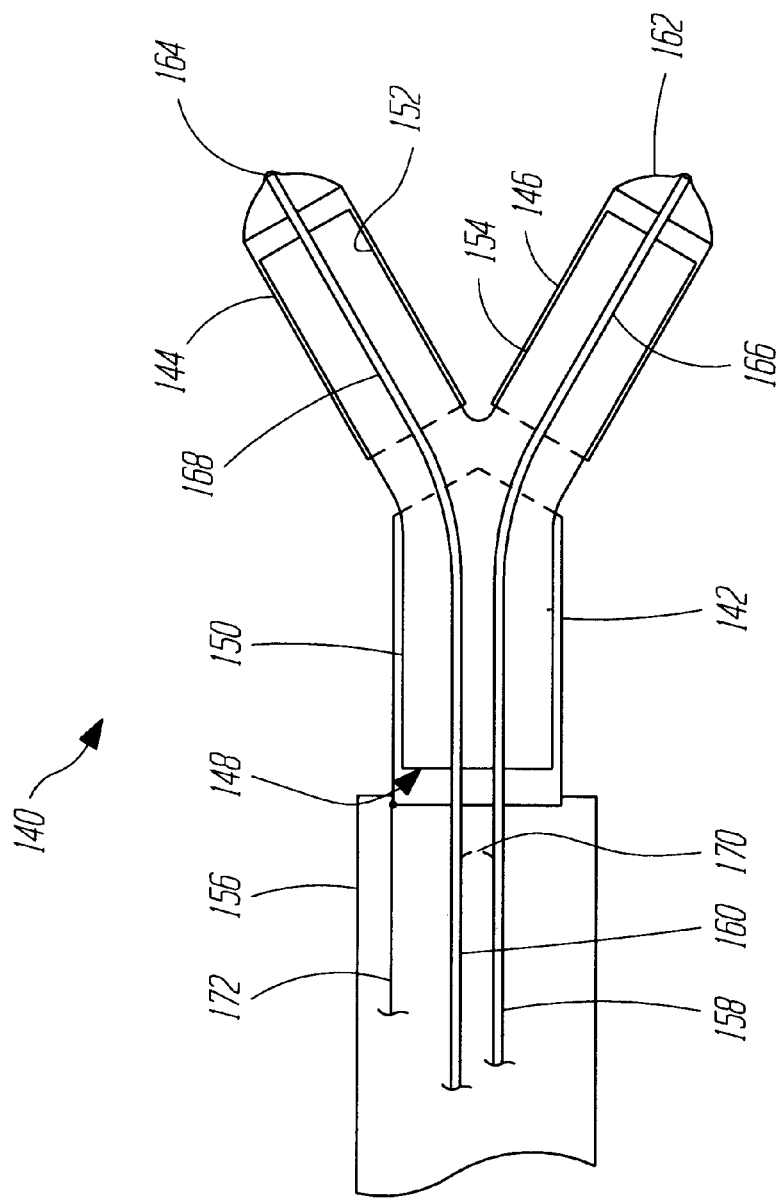

SYSTEM FOR DELIVERING BIFURCATION STENTS

BACKGROUND OF THE INVENTION

The present invention relates to a system for treating vascular disease. More specifically, the present invention relates to a system for deploying a stent in a bifurcation lesion. It is also contemplated that the present invention may be useful in AAA graft delivery.

Vascular disease currently represents a prevalent medical condition. Typical vascular disease involves the development of a stenosis in the vasculature. The particular vessel containing the stenosis can be completely blocked (or occluded) or it can simply be narrowed (or restricted). In either case, restriction of the vessel caused by the stenotic lesion results in many well known problems caused by the reduction or cessation of blood flow through the restricted vessel.

A bifurcation is an area of the vasculature where a first (or parent) vessel is bifurcated into two or more branch vessels. It is not uncommon for stenotic lesions to form in such bifurcations. The stenotic lesions can affect only one of the vessels (i.e., either of the branch vessels or the parent vessel) two of the vessels, or all three vessels.

Vascular stents are also currently well known. Vascular stents typically involve a tubular stent which is movable from a collapsed, low profile, delivery position to an expanded, deployed position. The stent is typically delivered using a stent delivery device, such as a stent delivery catheter. In one common technique, the stent is crimped down to its delivery position over an expandable element, such as a stent deployment balloon. The stent is then advanced using the catheter attached to the stent deployment balloon to the lesion site under any suitable, commonly known visualization technique. The balloon is then expanded to drive the stent from its delivery position to its deployed position in which the outer periphery of the stent frictionally engages the inner periphery of the lumen. In some instances, the lumen is predilated using a conventional dilatation catheter, and then the stent is deployed to maintain the vessel in an unoccluded, and unrestricted position.

Self-expanding stents can also be used. Self-expanding stents are typically formed of a resilient material. For example, some self-expanding stents are formed of a Nitinol material which is trained to deploy at body temperature. However, other resilient materials can also be used. The resilient material has sufficient resilience that it can be collapsed to the low profile position and inserted within a delivery device, such as a catheter. Once the catheter is placed at the site of the stenotic lesion, the stent is pushed from within the catheter such that it is no longer constrained in its low profile position. The stent, driven by the resilience of the material, expands to a higher profile, deployed position in which its outer periphery frictionally engages the walls of the stenosed vessel, thereby reducing the restriction in the vessel.

While there have recently been considerable advances in stent design and stent deployment techniques, deployment of stents in the treatment of bifurcation lesions remains problematic, particularly where both downstream branch vessels are affected by the lesion. Current techniques of dealing with such lesions typically require the deployment of a slotted tube stent across the bifurcation. However, this compromises the ostium of the unstented branch.

Further, once the first stent is deployed, the treating physician must then advance a dilatation balloon between the struts of the stent already deployed in order to dilate the second branch vessel. The physician may then attempt to maneuver a second stent through the struts of the stent already deployed, into the second branch vessel for deployment. This presents significant difficulties. For example, dilating between the struts of the stent already deployed tends to distort that stent. Further, deploying the second stent through the struts of the first stent is not only difficult, but it can also distort the first stent. Thus, the current systems used to alternately deploy stents in a bifurcated lesion have significant disadvantages.

SUMMARY OF THE INVENTION

A stent deployment system includes a tubular member having a first end and a second end and a generally longitudinal opening between the first and second ends. The tubular member has an inner periphery sized to receive a stent therein. A plurality of apertures are disposed on opposite sides of the generally longitudinal opening. An elongate retainer is removably receivable within the apertures to retain the stent in the tubular member and to release the stent from the tubular member when removed from the apertures.

BRIEF DESCRIPTION OF THE DRAWINGS

FIG. 1 illustrates a typical bifurcation lesion.

FIGS. 2A–2D illustrate one embodiment of a stent deployment system in accordance with one aspect of the present invention.

FIGS. 2E–2G illustrate various stents for use in the present invention.

FIGS. 10A–10D illustrate a stent deployment system in accordance with another aspect of the present invention.

DETAILED DESCRIPTION OF THE PREFERRED EMBODIMENTS

Figure 2C:
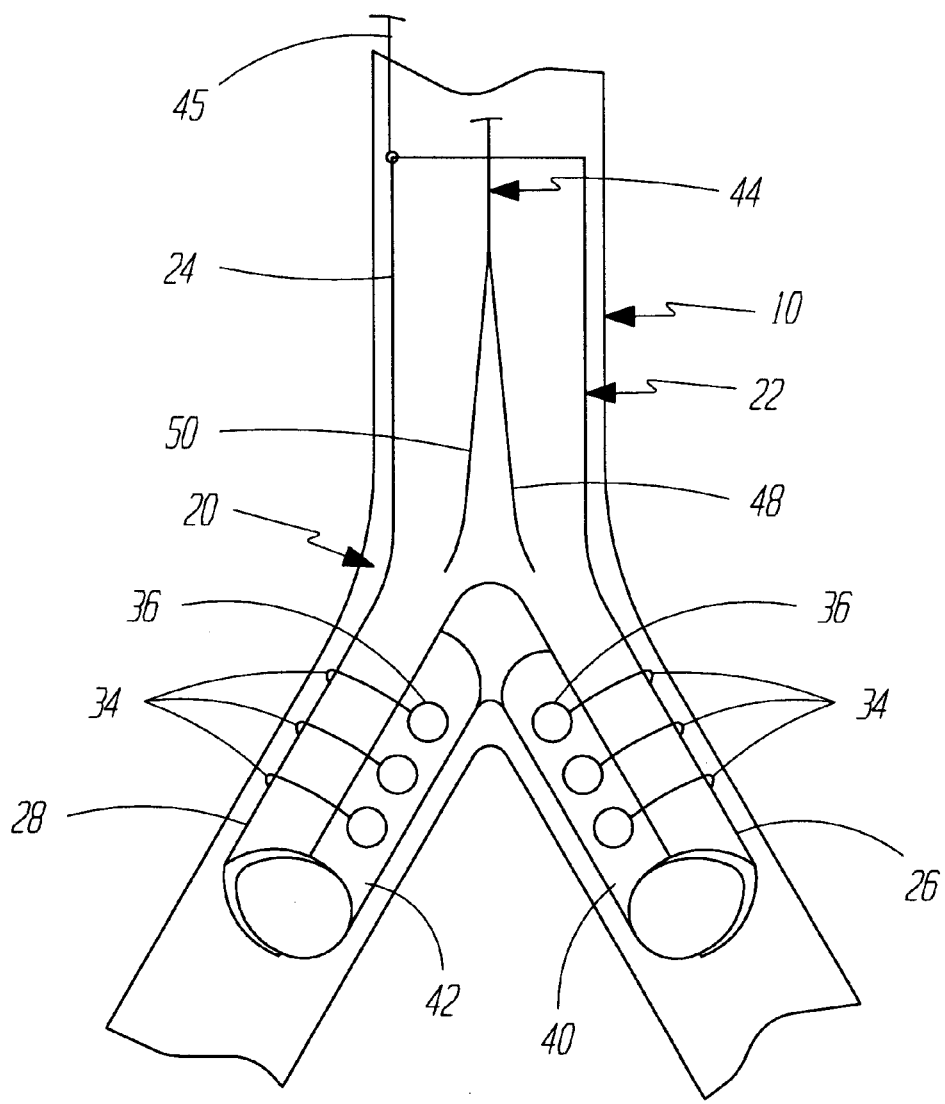

Although the present invention is described with specific reference to stents delivered to bifurcation lesions, it is also contemplated that the present invention may be applied to AAA graft delivery. For sake of clarity and for illustrative purposes only, the following detail description focuses on bifurcated stent delivery.

FIG. 1 illustrates bifurcation 10 which includes parent vessel 12, first branch vessel 14 and second branch vessel 16. FIG. 1 also illustrates that a bifurcation lesion 18 has developed in bifurcation 10. As illustrated, lesion 18 extends into both branch vessels 14 and 16, and extends slightly into parent vessel 12 as well. Lesion 18 may also be located on only one side of the branch vessel 14 or 16. In either case, it is preferable to stent both branch vessels 14 and 16 to avoid collapsing one. In order to treat bifurcation lesion 18, it may commonly first be predilated with a conventional angioplasty balloon catheter dilatation device.

FIGS. 2A–2D illustrate the operation of a stent deployment system 20 in accordance with one aspect of the present invention. System 20 includes a sheath 22 which has a trunk portion 24, a first branch portion 26 and a second branch portion 28. Sheath 22 also includes a proximal withdrawal member 43 which is attached, in one illustrative embodiment, to the proximal end of sheath 22. The withdrawal member 43 may be a tube, a wire, a continuation of the sheath 22, or any other suitable structure. In one illustrative embodiment, branch portions 26 and 28 include generally longitudinal openings or slits 30 and 32, respectively. In addition, in accordance with one illustrative embodiment, branch portions 26 and 28 of sheath 22 also include a plurality of containment rings 34, each of which have an eyelet 36 and 38 at opposite ends thereof. Rings 34 are disposed about the periphery of branch portions 26 and 28. In one illustrative embodiment, rings 34 are embedded in the material of branch portions 26 and 28 of sheath 22. In another illustrative embodiment, rings 34 are adhered to either the exterior or interior surface of the respective branch portions of sheath 22 by a suitable adhesive, by welding, or by other suitable connection mechanisms.

In the embodiment illustrated in FIG. 2A, branch portions 26 and 28 of sheath 22 each have, received therein, stents 40 and 42, respectively. Stents 40 and 42 may be used in conjunction with a trunk stent portion 41 as illustrated in FIG. 2E. It is also contemplated that stents 40 and 42 as illustrated in FIG. 2A may be replaced with bifurcated stents 210a or 210b as illustrated in FIG. 2F and FIG. 2G. However, any of the stents illustrated in FIGS. 2E–2G may be utilized with any of the delivery systems of the present invention. Each bifurcated stent 210a and 210b and their corresponding parts may be generically referred to as stent 210 or bifurcated stent 210. Preferably, bifurcated stent 210a is utilized. In the illustrative embodiment, stents 40 and 42 are self-expanding stents which are retained in a low profile, delivery position within branch portions 26 and 28, but which can be released from branch portions 26 and 28 to assume a higher profile, deployed position.

System 20 also includes an elongate release member 44. In one illustrative embodiment, release member 44 is simply a wire which has a proximal portion 46 and first and second branch portions 48 and 50, respectively. Branch portions 48 and 50, during delivery of legs 212 and 214 of bifurcated stent 210 or during delivery of stents 40 and 42, are threaded through eyelets 36 and 38 on each of rings 34 to hold the rings together in the lower profile delivery position, thus constraining stents 40 and 42 within branch portions 26 and 28 of sheath 22, respectively.

First branch portion 48 and second branch portion 50 may be threaded through eyelets 36 and 38 starting with the most proximal eyelets and extending to the most distal eyelets as illustrated in FIG. 2A. Alternatively, the branch portions 48 and 50 may be threaded through the most distal eyelets first. With this alternative arrangement, the branch portions 48 and 50 initially extend alongside the eyelets 36 and 38, then are threaded through the distal most eyelets and advanced to the proximal most eyelets. The alternative arrangement of the branch portions 48 and 50 causes the proximal portion of the branch portions 26 and 28 of the sheath 22 to open first. This arrangement is contemplated to provide a more accurate deployment of the stents 40, 42.

FIG. 2B is a greatly enlarged partial cross-sectional view of system 20, taken along section lines 2B—2B illustrated in FIG. 2A. FIG. 2B illustrates that eyelets 36 and 38, in the delivery position, overlap one another slightly to form an overlapping region 52. In the illustrative embodiment, branch portion 48 of retaining member 44 is threaded through overlapping region 52 to hold eyelets 36 and 38 together in the position shown in FIG. 2B. This causes ring 34 to contain branch portion 26 of sheath 22 in a lower profile position, thus holding stent 40 in the lower profile, delivery position.

For stent deployment, system 20 is advanced through the vasculature (preferably within a guide catheter) to bifurcation 10 with rings 34, and hence sheath portions 26 and 28, in the low profile, delivery position shown in FIG. 2B. Sheath 22 is then advanced from within the delivery catheter into the bifurcation 10. Once at the proper deployment site within bifurcation 10 (as shown in FIG. 2A) proximal portion 46 of retainment wire 44 is withdrawn proximally. This causes branch portions 48 and 50 of retaining wire 44 to be withdrawn proximally, and thus to be withdrawn from the overlapping regions 52 of eyelets 36 and 38 on containment rings 34. This allows eyelets 36 and 38 to separate from one another under the resilience of stent 40 then contained within the sheath.

FIG. 2C illustrates system 20 with retaining wire 44 withdrawn proximally to allow stents 40 and 42 to expand. As stents 40 and 42 expand, they drive sheath portions 26 and 28 open along slits 30 and 32, respectively.

Figure 2D:
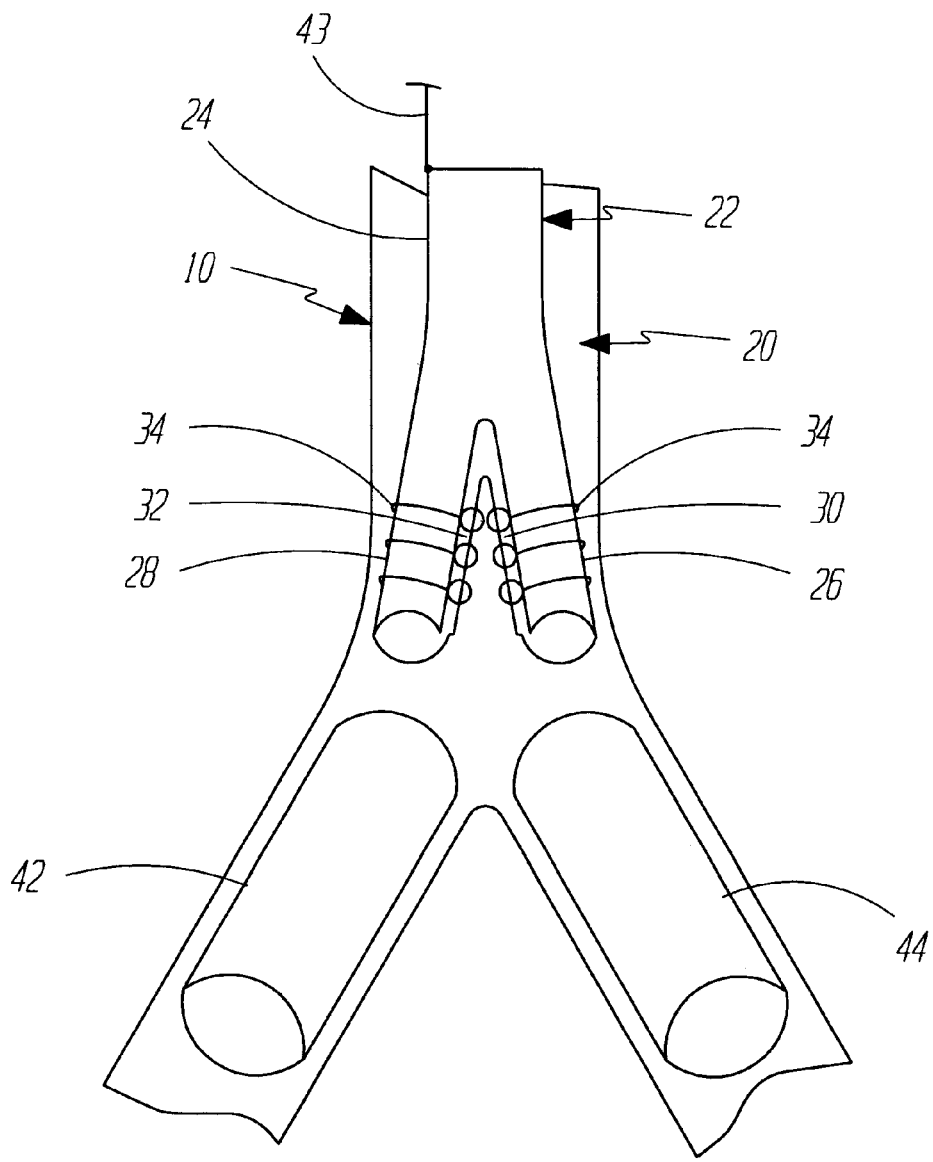

Withdrawal member 43 is then withdrawn proximally to pull sheath 22 proximally thereby leaving legs 212 and 214 of bifurcated stent 210 or stents 40 and 42 in the deployed position within the bifurcation. FIG. 2D illustrates system 20 in which sheath 22 has been withdrawn proximally, into the parent vessel 12 of bifurcation 10, leaving legs 212 and 214 of stent 210 or stents 40 and 42 in the deployed position within the bifurcation. Further withdrawal of member 43 causes deployment of the trunk members 41, 216a or 216b, depending on the type of stent utilized. System 20 can then be removed from the vasculature either within a delivery catheter, or separately therefrom.

Figure 3A:
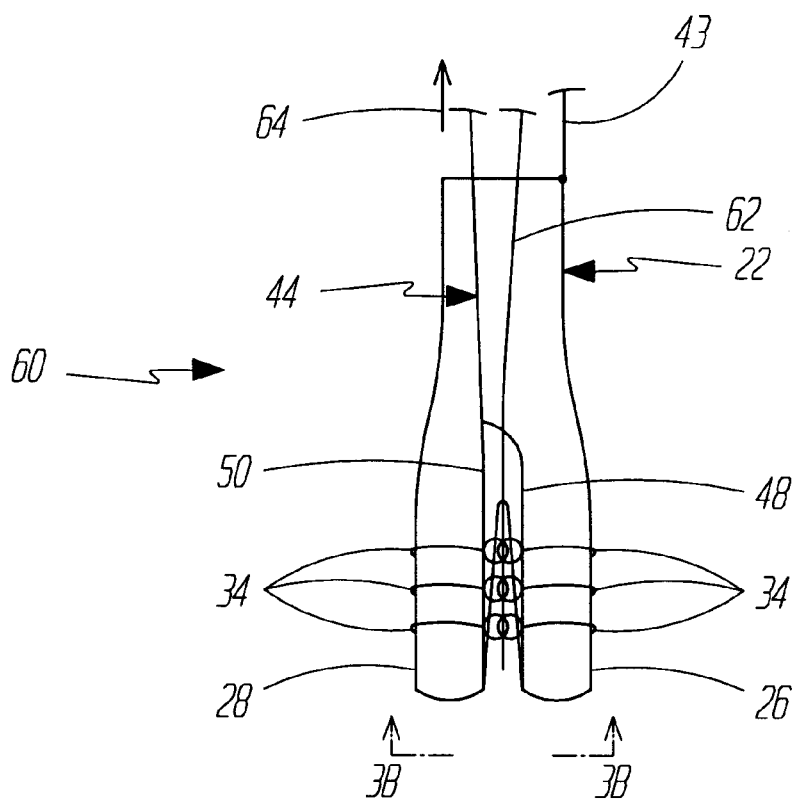
FIGS. 3A–3B illustrate another embodiment of a stent deployment system in accordance with one aspect of the present invention.

FIG. 3A illustrates another embodiment of a stent deployment system 60 in accordance with one aspect of the present invention. A number of items are similar to those shown in previous figures and they are similarly numbered. System 60 is formed such that branch sheaths 26 and 28 tend to assume the stent deployment position. In other words, the material is biased such that the distal ends of stents sheaths 26 and 28 tend to diverge from one another. However, system 60 is provided with a mechanism by which branch sheaths 26 and 28 can be maintained in an insertion position illustrated in FIG. 3A in which the branch sheaths are maintained closely adjacent one another. In the insertion position, system 60 can be advanced such that its distal end abuts, or is closely adjacent, bifurcation 10. Branch sheaths 26 and 28 are then deployed to a stent deployment position in which the branch sheaths assume the position shown in FIG. 2A in which the distal ends of the branch sheaths are separated from one another such that they more closely conform to the shape of bifurcation 10.

System 60 is provided with an additional elongate member, or wire, 62. In one illustrative embodiment, additional eyelets are provided along both of branch sheaths 26 and 28. When the branch sheaths are collapsed to the insertion position illustrated in FIG. 3A, the additional eyelets overlap one another. Elongate wire 62 is threaded through the additional eyelets to keep branch sheaths 26 and 28 in the collapsed position shown in FIG. 3A. However, when elongate wire 62 is withdrawn proximally in the direction indicated by arrow 64, the branch sheaths 26 and 28 are allowed to diverge from one another to the stent deployment position illustrated in FIG. 2A.

Figure 3B:
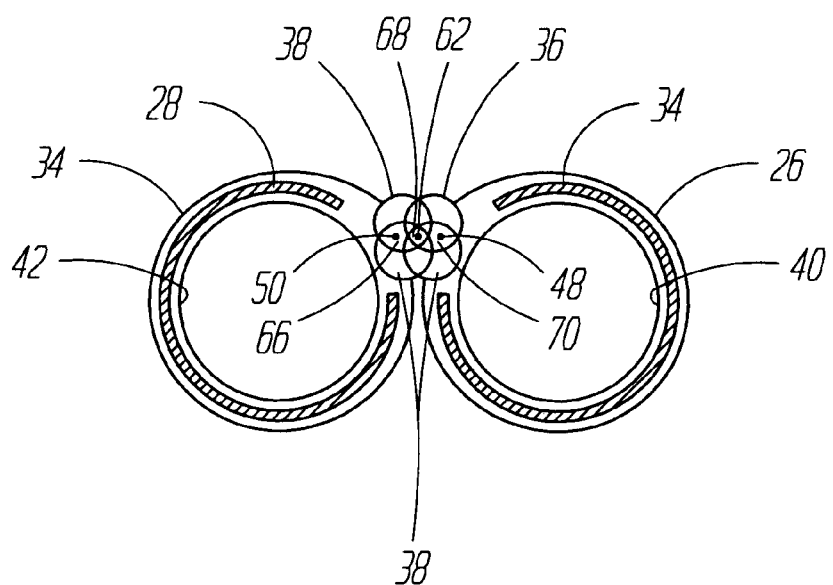

FIG. 3B is a greatly enlarged view of system 60 taken along lines 3B—3B illustrated in FIG. 3A and illustrating an embodiment in which eyelets 36 and 38 are used to maintain sheath 22 in the collapsed position illustrated in FIG. 3A. FIG. 3B illustrates branch sheaths 26 and 28 which are retained by rings 34. In one illustrative embodiment, the eyelets 36 and 38 attached to the ends of rings 34 are simply aligned to form three overlapping regions 66, 68 and 70. In overlapping regions 66 and 70, the branch portions 48 and 50 of retaining member 44 are threaded therethrough in order to maintain rings 34 in a retaining position about sheaths 26 and 28.

In addition, however, the eyelets 36 and 38 associated with rings 34 around both branch sheaths 26 and 28 also overlap one another in region 68. In that region, elongate wire 62 is threaded therethrough in order to maintain the branch sheaths 26 and 28 in close proximity to one another along substantially the entire longitudinal length thereof. Thus, when wire 62 is withdrawn from overlapping regions 68, branch sheaths 26 and 28 are allowed to resume their preformed position. Then, the distal ends of sheaths 26 and 28 are advanced into the branch vessels of bifurcation 10 and retaining member 48 is withdrawn from overlapping regions 66 and 70 allowing sheaths 26 and 28 to open, and thus allowing legs 212 and 214 of stent 210 or stents 40 and 42 to deploy in the branch vessels followed by deployment of trunk portion 41, 216a or 216b depending on the type of stent used.

Figure 4:
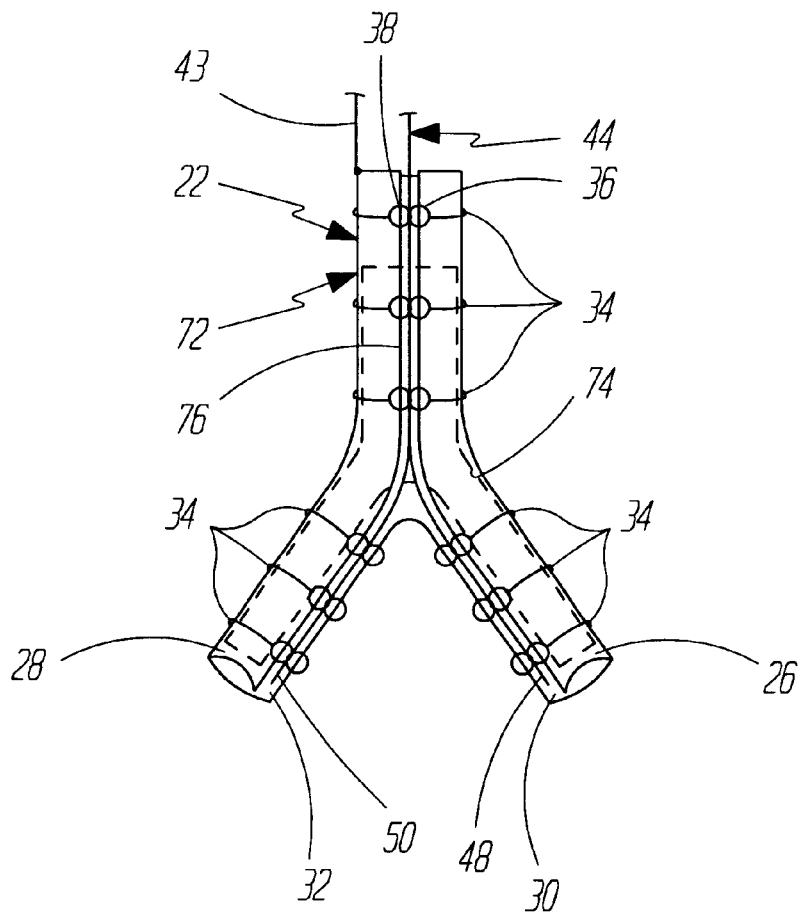
FIG. 4 illustrates another embodiment of a stent deployment system in accordance with the present invention.

FIG. 4 illustrates another embodiment of a stent delivery system in accordance with one aspect of the present invention. A number of items are similar to those shown in previous figures, and are similarly numbered. However, FIG. 4 illustrates a system 72 in which a bifurcated stent 74 (shown in phantom) is placed within sheath 22. In addition, sheath 22 is provided not only with elongate slits or openings 30 and 32 along branch sheaths 26 and 28, but it is also provided with a trunk slit or opening 76 which is provided along the trunk portion of sheath 22. A plurality of rings 34 are therefore also provided around the trunk portion 24 of sheath 22. Rings 34 are, as in previous embodiments, provided with eyelets 36 and 38 which overlap one another. Thus, elongate retaining wire 44 is also threaded through eyelets 36 and 38 attached to rings 34 about trunk portion 24 of sheath 22. When elongate retaining wire 44 is withdrawn proximally, not only do the branch portions 26 and 28 of sheath 22 allow deployment of the branch portions of stent 74, but the trunk portion allows deployment of the trunk portion of stent 74 as well. Sheath 22 is then withdrawn using withdrawal member 43 leaving stent 74 in place in bifurcation 10.

Figure 5:
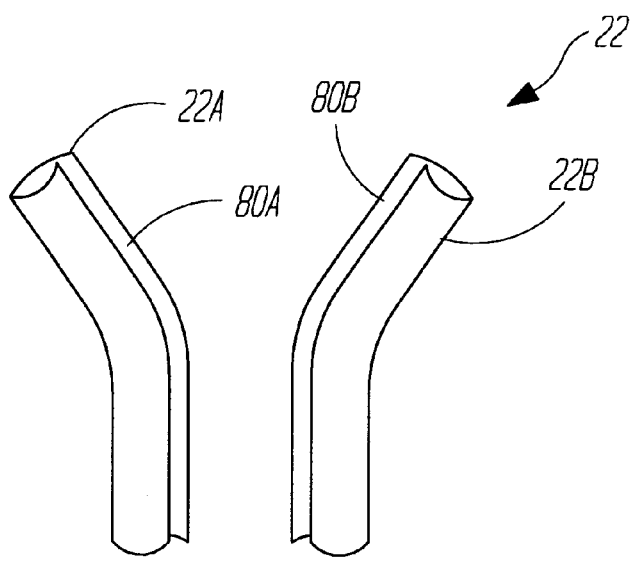
FIG. 5 illustrates the formation of a stent deployment sheath in accordance with one aspect of the present invention.

FIG. 5 illustrates one embodiment of the formation of sheath 22. In the embodiment illustrated in FIG. 5, sheath 22 is formed of a first section 22A and a second section 22B. Section 22A is simply formed as a rolled sheet which is stamped or preformed in the configuration illustrated in FIG. 5. When rolled as shown in FIG. 5, portion 22A has an elongate longitudinal slit 80A which runs substantially the entire longitudinal length thereof. Similarly, portion 22B is formed identically to portion 22A, but is simply oriented 180° relative to portion 22A. Thus, slits 80A and 80B are generally aligned opposing one another.

The trunk portions of slits 80A and 80B are then attached to one another, such as by heat fusing, a suitable adhesive, welding, or other suitable means, to form the sheath 22 as illustrated in FIG. 2A. Then, rings 34 are disposed about branch portions 26 and 28 of sheath 22. Alternatively, rings 34 can be embedded in the sheath material at any time during the formation process. Similarly, in order to obtain the embodiment illustrated in FIG. 4, only one edge of the trunk portion of slits 80A and 80B are fused to one another, leaving slit or opening 76 which extends along the trunk portion of sheath portion 22 as well.

It is also contemplated that the slits 80 and the rings 34 may be eliminated by embedding the branch portions 48 and 50 of the retaining wire 44 directly into the sheaths 22 along the preferred slit line. By pulling retaining wire 44 embedded in the sheath 22, the embedded wire tears the sheath to form the desired slits. The wire 44 including its branch portions 48 and 50 may be embedded in the branch sheaths 26 and 28 only, or in the trunk portion and branch portions.

Figure 6A:
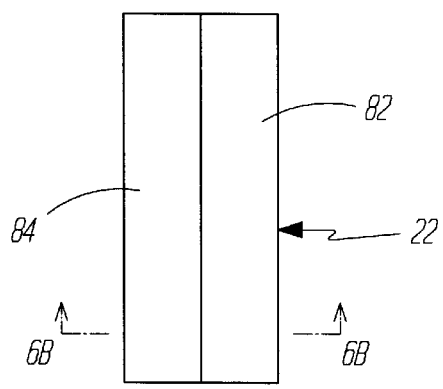
FIGS. 6A–6D illustrate the formation of a stent deployment sheath in accordance with another aspect of the present invention.
Figure 6B:
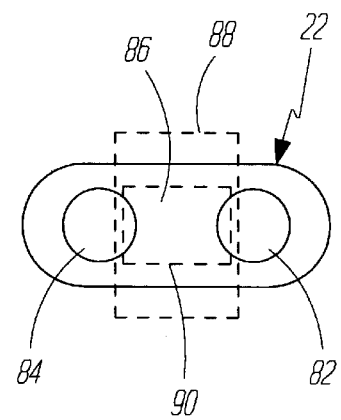

FIGS. 6A–6D illustrate the formation of sheath 22 in accordance with another aspect of the present invention. FIG. 6A generally illustrates that sheath 22 is first formed as a co-extruded, dual-lumen tube with first lumen 82 and second lumen 84. FIG. 6B is a cross-sectional view of the co-extruded tube illustrated in FIG. 6A, taken along section lines 6B—6B in FIG. 6A. FIG. 6B illustrates that first lumen 82 and second lumen 84 are separated by a septum 86. The dual extrusion can be done using any suitable technique.

Figure 6C:
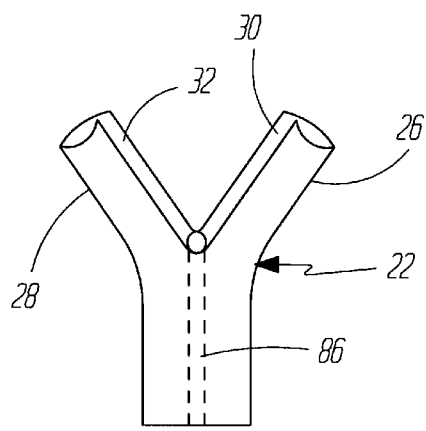

Once the dual lumen tube is formed, septum 86 is removed along the branch portions of sheath 22 in the area outlined by dashed line 88 in FIG. 6B. It should be noted that area 88 includes the entire septum, and also communicates with lumens 82 and 84. Thus, in the region of branch sheaths 26 and 28, enough of the septum is removed to form slits 30 and 32. Thus, sheath 22 is formed as shown in FIG. 6C, with septum 86 being completely removed from leg portions 26 and 28 of sheath 22.

Figure 6D:
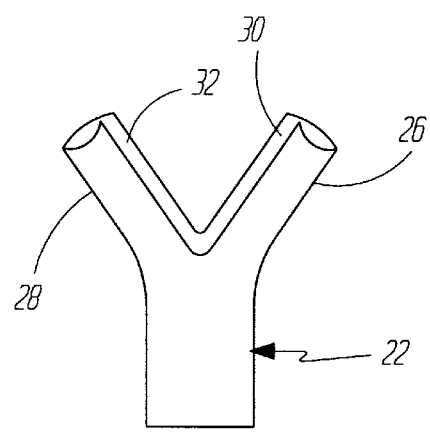

Septum 86 is then completely removed from the trunk portion of sheath 22 in the region identified by dashed line 90 in FIG. 6B. It should be noted that the region 90 does not extend all the way to the exterior periphery of sheath 22, as does area 86. Thus, there is no external slit running along the trunk portion of sheath 22. Instead, sheath 22 is formed as illustrated in FIG. 6D, with the trunk portion forming a cylinder. However, if it is desired that sheath 22 be formed as illustrated in the embodiment shown in FIG. 4, then region 90 can be expanded to extend along one edge of the trunk portion of sheath 22. This provides a slit extending along the trunk portion of sheath 22, as well as along the branch portions.

Figure 7:
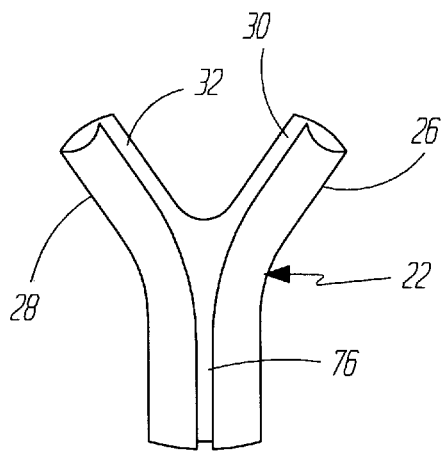
FIG. 7 illustrates the formation of a stent deployment sheath in accordance with another aspect of the present invention.

FIG. 7 illustrates another embodiment of sheath 22. Rather than forming sheath 22 as illustrated in the previous figures, sheath 22 shown in FIG. 7 is formed by simply stamping a single piece of material from sheath stock and rolling the material into the configuration shown in FIG. 7. It will be noted that the configuration shown in FIG. 7 provides slits 30, 32 and 76 which extend along the branch portions 26 and 28 of sheath 22 and which also extend along the trunk portion of sheath 22 as well. Of course, the edges which define slit 76 can be heat fused, or otherwise attached to one another, to eliminate slit 76.

Figure 8A:
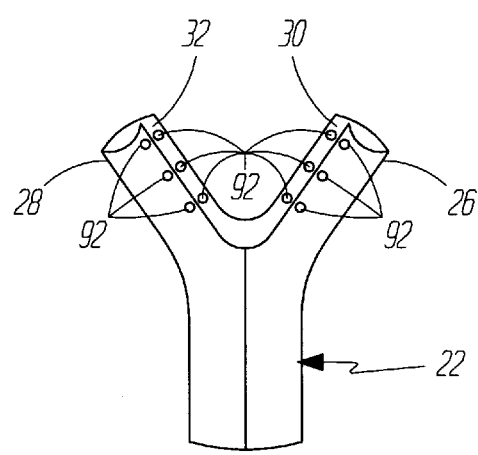
FIGS. 8A–8C illustrate a stent deployment sheath in accordance with another aspect of the present invention.
Figure 8B:
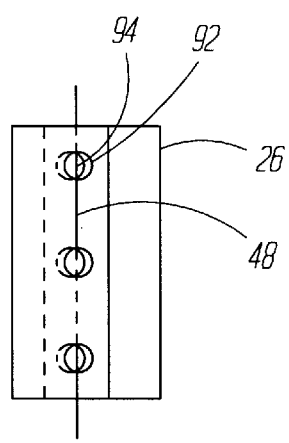
Figure 8C:
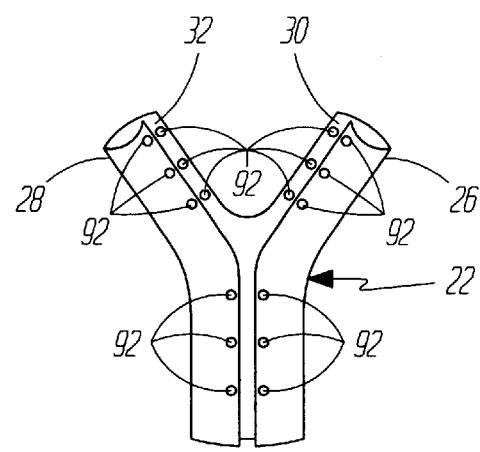

FIGS. 8A–8C illustrate the formation of sheath 22 in accordance with another aspect of the present invention. In the embodiment shown in FIGS. 8A–8C, sheath 22 is stamped from a single piece of stock material, such as shown in FIG. 7. However, sheath 22 is also provided with stamped, drilled, or cut apertures 92. Apertures 92 are disposed generally proximate slits 30 and 32 in the branch portions 26 and 28 of sheath 22. The slots 92 are generally aligned with one another along the edges of slots 30 and 32. Therefore, when slots 30 and 32 are rolled over one another, apertures 92 overlap one another, as shown in FIG. 8B, which is an enlarged view of a portion of branch 26.

With apertures 92 overlapping one another to form an overlap region 94, the branch portion 48 of retaining member 44 can be threaded through the overlapping regions 94 to retain the branch portion 26 of sheath 22 in a lower profile configuration, wrapped about stent 40. Branch portion 28 is similarly configured. When retaining member 48 is removed or withdrawn from overlapping regions 94, the branch portion 26 of sheath 22 is free to open, allowing the stent 40 retained therein to deploy in the branch vessel of bifurcation 10. Branch portion 28 is similarly manipulated to deploy stent 42.

FIG. 8C illustrates another embodiment in accordance with the present invention. The embodiment illustrated in FIG. 8C is similar to that shown in FIG. 8A in some respects. However, rather than having the slit in the trunk portion of sheath 22 fused, sheath 22 shown in FIG. 8C is provided with slit 76 similar to that shown in FIG. 7. In that embodiment, apertures 92 extend all the way from the distal tip of branch portions 26 and 28 of sheath 22 to a proximal end thereof and along the entire length of slit 76 in the trunk portion of sheath 22. Thus, elongate retaining member 44 can be threaded through the apertures in the trunk portion of sheath 22 as well. When elongate member 44 is withdrawn proximally, both the branch portions and the trunk portion of sheath 22 are allowed to open and release the stents therein, allowing the stents contained therein to deploy in the bifurcation 10.

Figure 9A:
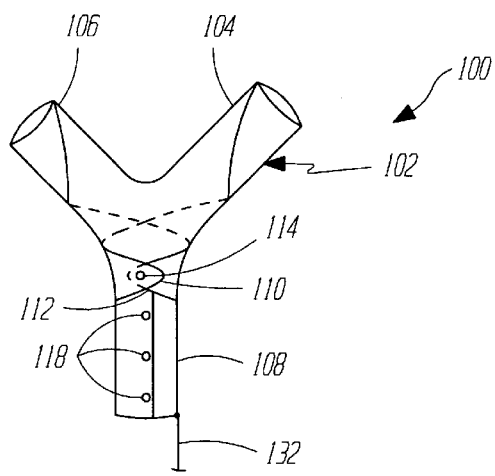
FIGS. 9A–9F illustrate the operation of a stent deployment sheath in accordance with another aspect of the present invention.

FIGS. 9A–9F illustrate stent deployment system 100 in accordance with one aspect of the present invention. FIG. 9A illustrates system 100 in a stent retaining, insertion position. System 100 includes a stent wrap 102 which has branch portions 104 and 106, and a trunk portion 108. Branch portions 104 and 106, as will be described in greater detail, are formed by wrapping a pre-formed flexible material, having ears 110 and 112, into the position illustrated in FIG. 9A.

Ears 110 and 112 have apertures 114 and 116 (only one of which is shown in FIG. 9A). Apertures 114 and 116 are disposed on ears 110 and 112 such that, when ears 110 and 112 are wrapped in the appropriate position, apertures 114 and 116 are generally aligned with, and overlie, one another.

Apertures 118 and 121 (only apertures 118 are shown in FIG. 9A) extend along trunk portion 108 of wrap 102. Apertures 118 and 121 are also generally aligned with, and overlie, one another when trunk portion 108 is wrapped as illustrated in FIG. 9A.

Thus, an elongate retaining member, such as member 44, can be threaded through apertures 114, 116, 118 and 121 to maintain wrap 102 in the stent retaining position illustrated in FIG. 9A. When withdrawn proximally, the retaining member 44 allows wrap 102 to unwrap and allows the stents to deploy within the bifurcation 10.

Figure 9B:
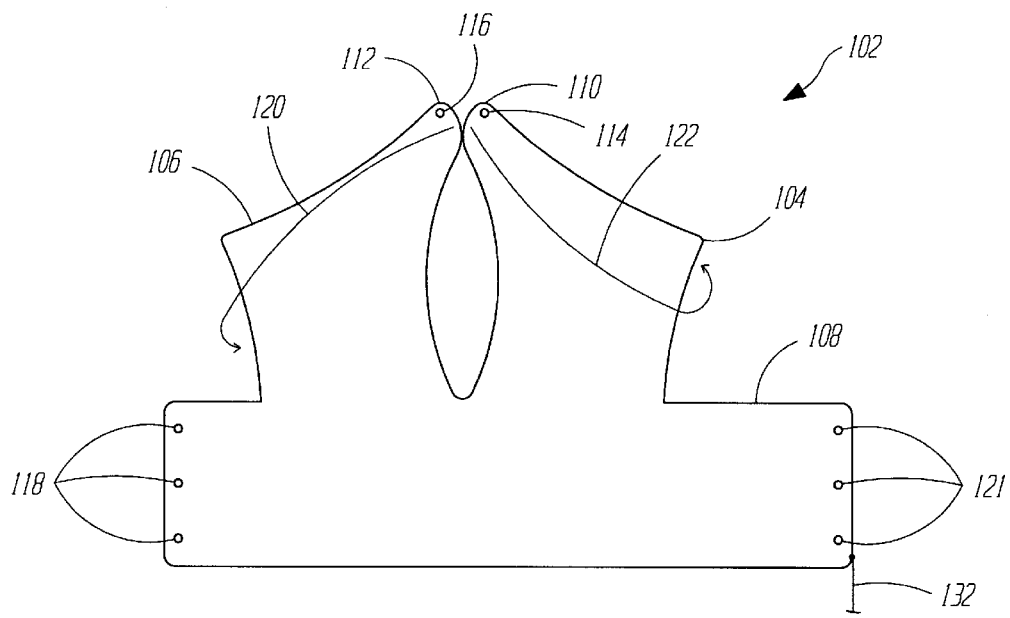
Figure 9C:
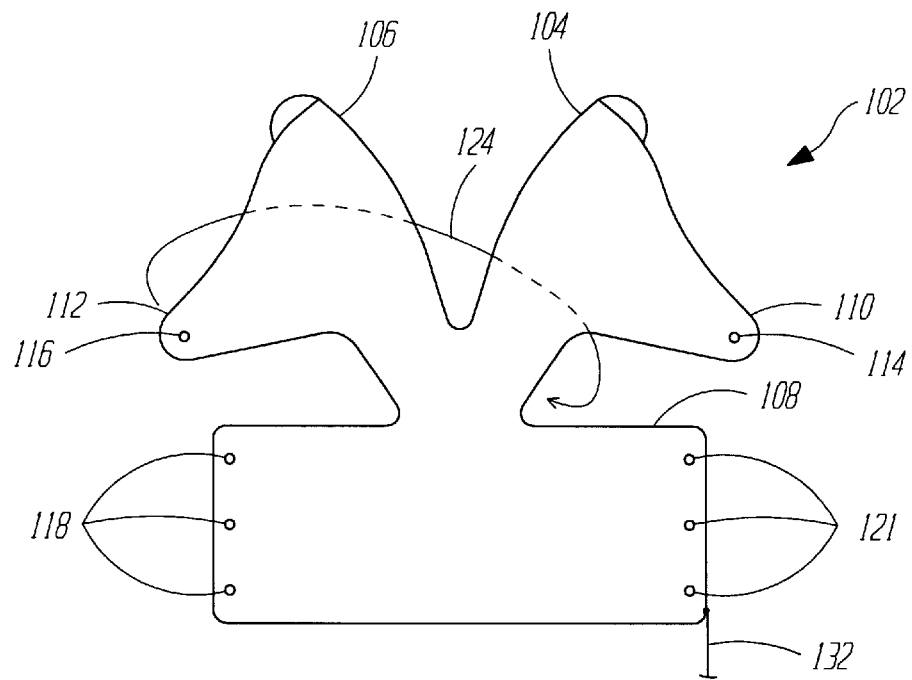
Figure 9D:
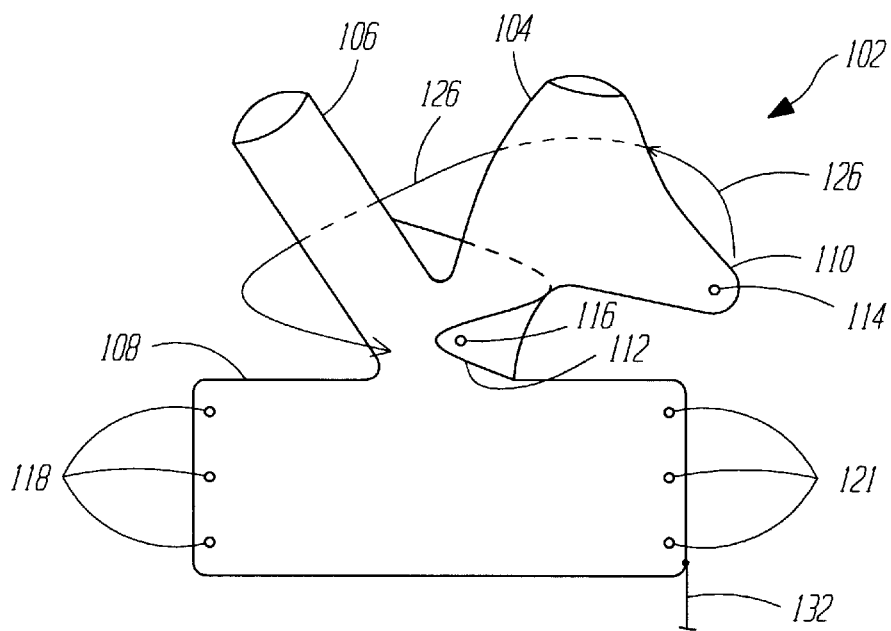
Figure 9E:
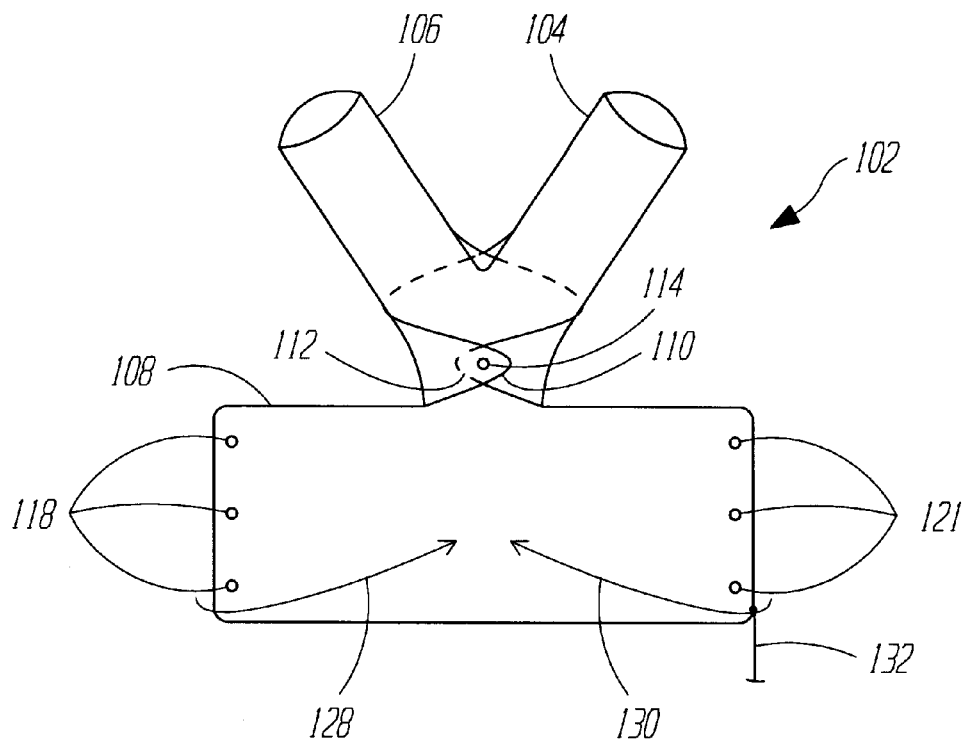

FIG. 9B illustrates prestamped wrap 102 in an unwrapped position. It can be seen that the trunk portion 108 of wrap 102 is simply formed in a generally rectangular conformation, which can be rolled such that apertures 118 and 121 are generally overlie one anther. In addition, branch portions 104 and 106 of wrap 102 extend away from trunk portion 108 and can be wrapped about stents to the conformation shown in FIG. 9A.

In order to perform such wrapping, ear 112 of portion 106 is first wrapped downwardly and about itself in the direction generally indicated by arrow 120. Next, ear 110 is wrapped in the same fashion, in the direction generally indicated by arrow 122. This results in the conformation generally illustrated in FIG. 9C.

Next, ear 112 is wrapped about the back portion of both leg portions 104 and 106 in the direction generally indicated by arrow 124. This results in the conformation generally illustrated in FIG. 9D.

Ear 110 is then wrapped in a similar fashion as ear 112, in the direction generally indicated by arrow 126. This results in the confirmation generally indicated in FIG. 9E, in which ears 110 and 112 overlap one another such that apertures 114 and 116 are generally aligned with one another.

Figure 9F:
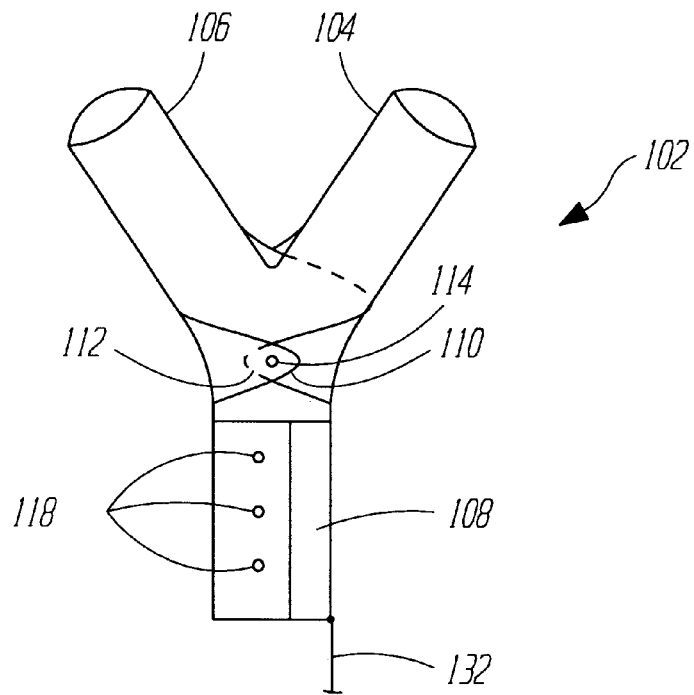

The two lateral edges of trunk portion 108 are then wrapped inwardly toward one another in the direction generally indicated by arrows 128 and 130. The edges are wrapped such that apertures 118 and 121 are in general alignment with one another as illustrated in FIG. 9F. Next, an elongate member (such as member 44) is threaded through apertures 114, 116, 118 and 121.

In one illustrative embodiment, wrap 102 is wrapped in this manner around a bifurcated stent, or individual stents, which are crimped down to the insertion position. Therefore, when the elongate member 44 is withdrawn from the apertures, wrap 102 is allowed to unwrap. The stent or stents are allowed to deploy in bifurcation 10.

It should be noted that, in one illustrative embodiment, wrap 102 is provided with a proximal withdrawal member 132. Withdrawal member 132 is attached to the proximal end of wrap 102. Withdrawal member 132 may be a wire, a tube, a continuation of trunk portion 108, or any other suitable structure. Thus, once the retaining member 44 is withdrawn from the apertures in wrap 102, elongate member 132 can be withdrawn proximally to remove the wrap 102 from the vasculature and to assist in deployment of the stents within the bifurcation 10.

It should also be noted that wrap 102, when wrapped about one or more stents, can be placed in a delivery catheter. Wrap 102 is then advanced, through or within the delivery catheter, to bifurcation 10 and then advanced from within the delivery catheter (such as by pushing on member 132) to a deployment position within bifurcation 10. The elongate member 44 is then withdrawn to deploy the stents as discussed above.

Figure 10B:
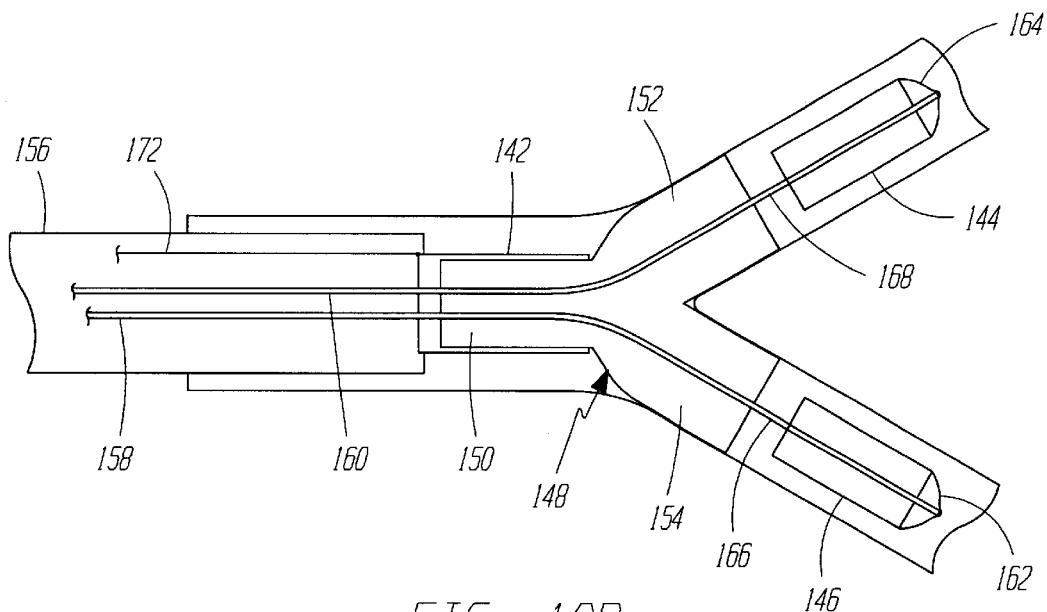

FIGS. 10A–10D illustrate a stent deployment system 140 in accordance with another aspect of the present invention. FIG. 10A illustrates system 140 in cross-section and shows that system 140, in one illustrative embodiment, includes a trunk delivery sheath 142 and a pair of branch delivery sheaths 144 and 146. System 140 is illustrated in FIGS. 10A–10D deploying a bifurcated stent 148 which includes a trunk portion 150 and two branch portions 152 and 154. System 140 is also illustrated in conjunction with catheter 156 which, in one illustrative embodiment, is a conventional guide catheter, or other catheter sized for use in delivering system 140 to bifurcation 10.

System 140 also includes, in one illustrative embodiment, a pair of elongate branch deployment members 158 and 160. Elongate members 158 and 160 are preferably guidewire tubes defining a guidewire lumen therein for advancement over a conventional guidewire (not shown). Catheter 156 and elongate members 158 and 160 may be formed of a braided tube to provide sufficient pushability. In one illustrative embodiment, branch deployment member 158 is attached to a distal flexible tip 162 on branch delivery sheath 146. Elongate deployment member 160 is attached to a distal flexible tip 164 on branch delivery sheath 144. In one alternative embodiment, only a single proximal elongate deployment member (158 or 160) is provided, and the distal ends 166 and 168 of deployment members 158 and 160, respectively, are attached to one another, such as at branching point 170. In this alternative embodiment, distal portions 166 and 168 may be in the form of a wire or other suitable structure.

In any case, system 140 is also, in one illustrative embodiment, provided with a proximal sheath delivery member 172 which is attached to the proximal end of trunk delivery sheath 142. Delivery member 172 may be in the form of a wire, tube, a continuation of trunk portion 142, or any other suitable structure. Preferably, delivery member 172 is a braided tube or similar structure. Each of the deployment sheaths 142, 144 and 146 preferably have an outer peripheral dimension which fits within the inner peripheral dimension of catheter 156. In addition, the inner peripheral dimension of sheaths 142, 144 and 146 is preferably suitable to receive the respective portions of stent 150, when stent 150 is in the low profile, delivery position.

In operation, sheaths 142, 144 and 146 are preferably withdrawn within the distal end of catheter 156 after stent 148 is placed therein. Catheter 156 is then advanced to the site of bifurcation 10 within the vasculature. Sheaths 142, 144 and 146 are then advanced out through the distal end of catheter 156 by providing a pushing force on elongate member 172. Alternatively, catheter 156 may be advanced having sheath 142 protruding out the distal end of catheter 156 such that elongate member 172 is pulled proximally rather than pushed distally. Next, either simultaneously, or sequentially, branch sheaths 144 and 146 are advanced distally using elongate members 158 and 160.

Since system 140 is located in the bifurcation 10, the branching portion of stent 148 engages the bifurcation 10 such that stent 148 is held in place within the vasculature. Sheaths 144 and 146 are then advanced further until they are advanced completely distally of the branch portions 152 and 154 of stent 148. This allows the branch portions 152 and 154 to deploy to the radially expanded position illustrated in FIG. 10B. In the higher profile deployed position, branch members 152 and 154 of stent 148 expand such that they frictionally engage the interior periphery of the branch vessels in bifurcation 10, thus anchoring stent 148 in place.

Figure 10C:
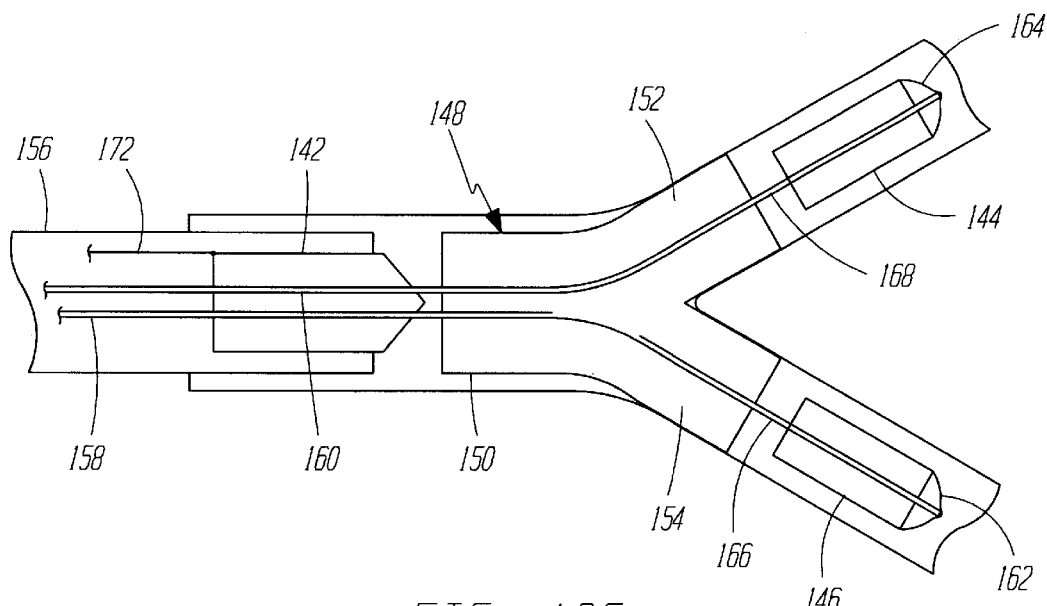

Elongate member 172 is then withdrawn proximally. This causes sheath 142 to be withdrawn proximally as well. Since stent 148 is anchored in place by branch portions 152 and 154, stent 148 remains in place while sheath 142 is withdrawn proximally. This allows sheath 142 to be drawn completely proximally of the proximal end of the trunk portion 150 of stent 148, thereby allowing trunk portion 150 to expand to the deployed position as illustrated in FIG. 10C. Stent 148 is thus completely deployed within the bifurcation 10.

Figure 10D:
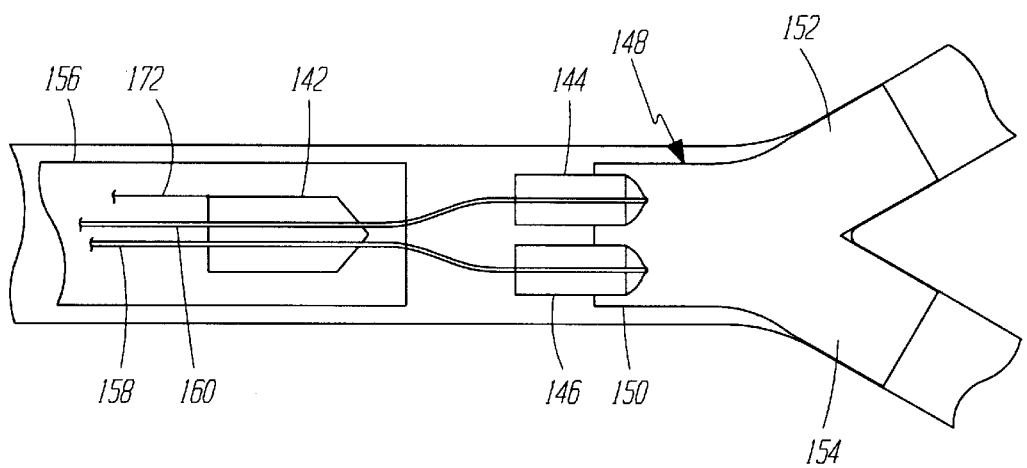

Next, elongate members 158 and 160 are withdrawn proximally such that sheaths 144 and 146 are also withdrawn proximally. In the illustrative embodiment illustrated in FIGS. 10A–10D, the external periphery of sheaths 144 and 146 is small enough such that it easily fits within the interior periphery of stent 148, once stent 148 is in the higher profile, deployed position. Therefore, as elongate members 158 and 160 are withdrawn proximally, sheaths 144 and 146 are withdrawn through the interior of stent 148 and within the interior of catheter 156. This is illustrated by FIG. 10D. System 140 is then removed from the vasculature, leaving stent 148 fully deployed.

It should be noted that, while the previous discussion has proceeded with respect to the stents being self-deploying stents, the stents can also be non-self-deploying stents. For instance, where the stents are self-deploying stents, they can be formed of a Nitinol or other suitably resilient material which is trained or otherwise disposed to deploy at body temperature to the higher profile position. However, the stents can also be crimped down over balloons such that, once placed in a suitable position in the bifurcation, the stents can be deployed by inflating the balloons, in a known manner.

In any case, the present invention provides a system for deploying a bifurcated stent which is highly advantageous over prior systems.

Although the present invention has been described with reference to preferred embodiments, workers skilled in the art will recognize that changes may be made in form and detail without departing from the spirit and scope of the invention.

What is claimed is:

1. A stent deployment system, comprising:
    a tubular member having a first end and a second end and a generally longitudinal opening between the first and second ends, the tubular member having an inner periphery sized to receive a stent therein and further comprising
        a first branch portion,
        a second branch portion, and
        a trunk portion coupled to the first and second branch portions;
    a stent received within the inner periphery of the tubular member;
    a plurality of apertures disposed on the tubular member; and
    an elongate retainer removably receivable within the apertures to retain the stent in the tubular member and to release the stent from the tubular member when removed from the apertures.

2. The stent deployment system of claim 1 wherein the first and second branch portions each include a generally longitudinal opening with a plurality of apertures disposed on opposite sides thereof and wherein the retainer includes a first elongate portion removably receivable within the apertures on the first branch portion and a second elongate portion removably receivable within the apertures on the second branch portion.

3. The stent deployment system of claim 2 wherein the first and second branch portions have distal ends and are biased in an expanded position in which the distal ends tend to separate from one another.

4. The stent deployment system of claim 3 wherein the retainer is configured to selectively retain the first and second branch portions in a collapsed position in which the distal ends thereof are located closely proximate one another.

5. The stent deployment system of claim 4 wherein the retainer includes a third elongate portion removably receivable within the apertures on the first and second branch portions to retain the first and second branch portions in the collapsed position.

6. The stent deployment system of claim 1 and further comprising:
a plurality of rings fixedly connected to the tubular member and defining the plurality of apertures.

7. The stent deployment system of claim 6 and further comprising:
a plurality of support members having first and second ends and an elongate portion, the elongate portion extending around the tubular member and each of the ends being fixedly coupled to one of the plurality of rings.

8. The stent deployment system of claim 7 wherein the tubular member includes a wall portion and wherein the support members are embedded in the wall portion of the tubular member.

9. The stent deployment system of claim 1 wherein the tubular member comprises:
a first elongate tube having a first trunk portion and a first branch portion; and
a second elongate tube having a second trunk portion and a second branch portion, the first and second trunk portions being connected to one another to form a single trunk, and the first and second branch portions being pre-formed in an expanded formation in which the first and second branch portions tend to diverge from one another.

10. The stent deployment system of claim 1 wherein the tubular member comprises:
a coextruded, dual lumen tube having first and second separated branch portions and a single lumen trunk portion.

11. The stent deployment system of claim 1 wherein the tubular member comprises:
a single sheet of material pre-formed into a bifurcated tubular member having a trunk portion and first and second branch portions.

12. The stent deployment system of claim 1 wherein the tubular member comprises:
a trunk portion and first and second branch portions sized to receive a bifurcated stent therein, and wherein the retainer includes a single elongate member removable from the apertures to release the bifurcated stent from the first and second branch portions and the trunk portion.

13. The stent deployment system of claim 1 wherein the tubular member comprises:
a single sheet of pliable material foldable into a stent receiving shape having a trunk portion and first and second branch portions, the longitudinal opening being disposed at least on the trunk portion when the sheet is folded into the stent receiving shape.

14. The stent deployment system of claim 1 and further comprising:
an elongate delivery member configured for delivery of the tubular member through vasculature to a stent deployment site.

15. The stent deployment system of claim 1 and further comprising:
an elongate removal member, coupled to the tubular member, and actuable to remove the tubular member from a deployment site at which the stent is deployed.

16. A stent deployment system, comprising:
a sheet of pliable material foldable into a stent receiving shape having a trunk portion and first and second branch portions; and
a retainer disposed relative to the sheet to selectively retain the sheet in the stent receiving shape and release the sheet from the stent receiving shape.

17. The stent deployment system of claim 16 wherein the sheet includes a plurality of apertures arranged to be generally aligned with one another when the sheet is in the stent receiving shape and wherein the retainer includes an elongate member receivable within the apertures to maintain the sheet in the stent receiving shape and removable from the apertures to release the sheet from the stent receiving shape.

18. A stent deployment system, comprising:
a first branch sheath sized to receive a stent;
a second branch sheath sized to receive a stent; and
an elongate deployment actuator, coupled to the first and second branch sheaths and actuable to move the first and second branch sheaths from a stent retaining position to a stent deploying position.

19. The stent deployment system of claim 18 and further comprising:
a trunk sheath sized to receive a stent and coupled to the elongate stent deployment actuator, the elongate stent deployment actuator being actuable to move the trunk sheath from a stent retaining position to a stent deploying position.

20. The stent deployment system of claim 19 and further comprising:
a stent having a trunk portion disposed within the trunk sheath and first and second branch portions disposed within the first and second branch sheaths, respectively, the stent being movable between a low profile delivery position and an expanded deployed position.

21. The stent deployment system of claim 20 wherein the elongate deployment actuator comprises:
a first elongate member coupled to the trunk sheath; and
an elongate branch deployment actuator coupled to the first and second branch sheaths.

22. The stent deployment system of claim 21 wherein the elongate branch deployment actuator comprises:
a second elongate member coupled to the first branch sheath; and
a third elongate member coupled to the second branch sheath.

23. The stent deployment system of claim 21 wherein the elongate branch deployment actuator comprises:
a first elongate portion extending within the first branch sheath and coupled to a distal end thereof; and
a second elongate portion extending within the second branch sheath and coupled to a distal end thereof.

24. The stent deployment system of claim 23 wherein the first and second branch sheaths are sized to be withdrawn through the stent when the stent is in the deployed position.

25. The stent deployment system of claim 20 wherein the stent comprises:
a single bifurcated stent.

26. The stent deployment system of claim 20 wherein the trunk portion and the first and second branch portions each comprise separate stents.

27. The stent deployment system of claim 20 wherein the first and second branch portions comprise:
a single articulated stent.

28. A method of deploying a stent at a stent deployment site in a bifurcation within vasculature, the method comprising:
providing a stent having first and second branch portions disposed within first and second branch sheaths;

advancing the first and second branch sheaths, with the first and second branch portions of the stent disposed therein, within the bifurcation;

advancing the first and second branch sheaths distally off of the first and second branch portions of the stent exposing the branch portions of the stent to the vasculature; and deploying the first and second branch portions in the bifurcation.

29. The method of claim 28 wherein the stent includes a trunk portion coupled to the first and second branch portions of the stent and disposed within a trunk sheath, and further comprising:

withdrawing the trunk sheath proximally of the trunk portion of the stent exposing the trunk portion of the stent to the vasculature; and deploying the trunk portion of the stent.

30. The method of claim 39 and further comprising:

withdrawing the first and second branch sheaths proximally through the deployed first and second branch portions of the stent.

31. The method of claim 30 and further comprising:

withdrawing the first and second branch sheaths proximally through the deployed trunk portion of the stent.

* * * * *